United States Patent [19]

Cerami et al.

[11] 4,247,533

[45] Jan. 27, 1981

[54] HEMOGLOBIN $A_{1c}$ RADIOIMMUNOASSAY

[75] Inventors: Anthony Cerami; Ronald J. Koenig, both of New York, N.Y.; Jamshid Javid, Old Tappan, N.J.; Penelope K. Pettis, Norwalk, Conn.

[73] Assignee: The Rockefeller University, New York, N.Y.

[21] Appl. No.: 901,618

[22] Filed: May 1, 1978

[51] Int. Cl.³ .................. G01N 33/48; G01T 1/00; B65D 71/00

[52] U.S. Cl. .................................. 424/1; 422/61; 424/12; 23/230 B

[58] Field of Search .................. 424/1, 1.5, 12; 206/569; 23/230 B; 422/61

[56] References Cited
PUBLICATIONS

Gabbay et al., J. Clin. End. Met., vol. 44, No. 5, May 1977, pp. 859-864.

Garver et al., Chem. Abstracts, vol. 83, Sep. 1, 1975, Abstract No. 75030g.

*Primary Examiner*—Benjamin R. Padgett
*Assistant Examiner*—Christine M. Nucker
*Attorney, Agent, or Firm*—Haight, Rosfeld, Noble & Santa Maria

[57] ABSTRACT

Sheep antiserum developed against the human glycohemoglobin, Hb $A_{1c}$, distinguishes this fraction from the major component Hb $A_o$. Partial cross relativity is observed with Hb $A_{1a}$ and Hb $A_{1b}$, as well as with analogous glycohemoglobins from mouse and dog hemolysates. The reactivity of the hemoglobins with this specific antiserum is abolished by the reduction of the keto group of the sugar ligand. The immunological specificity displayed provides the basis of a quantitative assay for Hb $A_{1c}$, which is suitable for studies of clinical and experimental diabetes.

11 Claims, No Drawings

HEMOGLOBIN A$_{1c}$ RADIOIMMUNOASSAY

BACKGROUND OF THE INVENTION

The present invention was wholly or partially made with funds provided by the Department of Health, Education and Welfare. Accordingly, the U.S. Government has a royalty free license under any patent granted with respect to this invention.

Hemoglobin (Hb) A$_{1c}$ is a glycohemoglobin with an amino acid structure which is identical to that of Hb A; the only detectable difference is the presence of 1-amino-1-deoxy-fructose attached in the 2,3-diphosphoglycerate pocket to the N-terminal valine in the beta-chain of Hb A$_{1c}$. The modification of Hb A to form Hb A$_{1c}$ is a continuous post-translational process, the rate of which is a function of the blood glucose concentration. The level of Hb A$_{1c}$ therefor reflects the status of the individual's carbohydrate metabolism. Normal adults have about 90% of their total hemoglobin as A$_o$, 2-3% as A$_{1a}$ and A$_{1b}$ and 3-6% of their total hemoglobin as Hb A$_{1c}$ whereas the range in juvenile and maturity onset diabetics is 6-15% as Hb A$_{1c}$. A similar increase in Hb A$_{1c}$ concentration has been noted in mice with genetic and chemically induced diabetes and in pancreatectomized dogs.

Diabetes mellitus has been found to occur naturally or can be induced in virtually every species in the animal kingdom. Greater insight into human diabetes can be gained by studying this disease process in animals whose diabetes closely resembles the human condition. Such animal models include the diabetic dog and mouse; see R. Engerman et al. Diabetes 26: 760–769; K. P. Hummel et al. in Science 153: 1127–1128 (1966); and A. A. Like et al. in Am. J. Pathol. 66: 193–204 (1927). Both of these species demonstrates increased levels of Hb Al$_{1c}$ in the diabetic state: (Koenig and Cerami: Proc. Natl. Acad. Sci. USA 72: 3687–91 (1975) and Koenig, unpublished data.)

These animal hemoglobins A$_{1c}$ cross-react sufficiently with the human Hb A$_{1c}$ antibody described herein so that their concentrations may be determined accurately by this RIA method. An RIA for animal Hb A$_{1c}$ is very useful because this technique requires only microgram quantities of hemoglobin, compared to milligrams for the widely used prior art column chromatographic method of Trivelli et al. described in New Engl. J. Med. 284: 353-7 (1971). RIA techniques for animal Hb A$_{1c}$ are thus useful in facilitating the evaluation of new drugs and other forms of therapy designed to treat human diabetes and accordingly should facilitate research into the basic pathophysiology of this disease.

Recent studies have indicated that the quantification of Hb A$_{1c}$ concentration is a useful means of assessing carbohydrate intolerance as well as adequacy of control in patients with diabetes: see Koenig et al. in New England J. Med. 295: 417–420 (1976). One of the difficulties in applying this measurement to clinical studies has been the technical problem of assaying Hb A$_{1c}$ in a large number of samples with the column chromatography method currently available which has been described by Trivelli et al. in New England J. Med. 284: 353–357 (1971). In order to circumvent this obstacle, we have studied the immunological properties of Hb A$_{1c}$ with a specific antiserum. The present invention applies these results to the radioimmunoassay of glycohemoglobins.

OBJECTS OF THE INVENTION

Accordingly, it is a general object of the present invention to provide an improved method for assaying hemoglobin A$_{1c}$.

Another object of the present invention is to provide anitbodies which are highly specific to hemoglobin A$_{1c}$ as an antigen, even in the presence of other, very similar antigens.

Another object of the present invention is to provide an improved test for hemoglobin A$_{1c}$ which enables a single person in one day to conduct 30–40 tests more readily than he could run the 2 or 3 tests per day in accordance with prior art methods.

Yet another object of the present invention is to provide immunological assay for hemoglobin A$_{1c}$ which exhibits high specificity with respect to the particular hemoglobin, yet has sufficient species cross-reactivity to facilitate its use for the study of diabetes in experimental animals.

Other objects, features and advantages of the present invention will become more fully apparent to those skilled in the art to which the invention pertains from the following specification and claims.

SUMMARY OF THE INVENTION

Briefly, the above and other objects, features and advantages of the present invention are attained in one aspect thereof by providing antibodies against human hemoglobin A$_{1c}$ which are substantially free of cross-reactivity against the human hemoglobin A$_o$, A$_{1a}$ and A$_{1b}$.

In a second aspect, the present invention provides a radioimmunoassay method for detecting hemoglobin A$_{1c}$ which comprises reacting a blood or other body fluid sample with said antibodies and determining the presence of an antigen-antibody complex by radioimmunoassay.

In a third aspect, the present invention provides an improved technique for the diagnosis of diabetes and other related diseases associated with elevated blood glucose levels by correlating the levels of hemoglobin A$_{1c}$; the method is especially suited for radioimmunoassay and sequentially reacts the antibodies with the test antigen alone, followed by reaction with the index antigen for a short period of time, e.g. about 0.5 hour at incubation temperatures from room temperature to about 37° C.

In a fourth aspect, the present invention provides a method for preparing such antibodies which comprises administering an antigenically effective amount of hemoglobin A$_{1c}$ antigen to an animal capable of producing antibodies thereto, preferably to an animal whose metabolism does not naturally form hemoglobin A$_{1c}$, and collecting said antibodies from the animal.

DETAILED DISCUSSION

Because the transformation of hemoglobin A into hemoglobin A$_{1c}$ is a function of glucose concentration in the blood, there is a great need for a quantitative assay method which is rapid and easily conducted without prohibitively expensive equipment. By virtue of certain species cross-reactivity discussed hereinafter, the provision of such a test in accordance with the present invention now provides an additional tool for the study of diabetes and similar diseases causing an elevation in blood glucose concentration in standard laboratory animals.

Highly specific antisera have been prepared that can recognize single amino acid substitutions in human hemoglobin by the radioimmunoassay (RIA) method, e.g. see Javid and Pettis in J. Lab. Clin. Med. 88: 621–626 (1976); Rowley et al. in Blood 43: 607–611 (1974); and Garver et al. in Science 196: 1334–36 (1977). Differences between the structure of the hemoglobin used for immunization and that of the immunized animal's own hemoglobin largely determine the specificities of the antibodies produced. While a wide variety of different species can be employed as the immunized animal for preparing antibodies to hemoglobin $A_{1c}$, it is presently preferred to immunize an animal whose metabolism does not naturally form hemoglobin $A_{1c}$, e.g. the cat, goat, sheep, etc. Sheep hemoglobin does not react with 2,3-diphosphoglycerate and may lack the configuration of the "DPG pocket" which permits the glycosylation of the beta-chain N-terminus. Indeed, glycosylated hemoglobin cannot be demonstrated in sheep red cell hemolysates. The sheep, then, apparently recognizes the N-terminus of the human Hb $A_{1c}$ as antigenic. The immunodominant feature of this antigenic determinant must require the spatial conformation provided by 1-amino-1-deoxyfructose. Reduction of the keto group strikingly and selectively reduces the reactivity with anti-$A_{1c}$, while leaving the affinity of other determinants for anti-A unaffected. The ability of the antibody to distinguish between a ketone and an alcohol might in fact reflect its ability to recognize a ring structure, since the keto moiety could readily form a hemiketal with the hydroxyl group of either carbon 5 or 6. The cross reaction of Hb $A_{1a}$ and Hb $A_{1b}$ with the antibody made to human Hb $A_{1c}$ is of interest since both molecules are probabaly glycohemoglobins. An exact structure has not been assigned to these hemoglobins.

Dog and mouse Hb $A_{1c}$ react less well than their human counterparts. This observation suggests that the steric fit of the antibody includes more than the sugar molecule and probably extends to surface features of the protein adjacent to it.

The specific immunologic recognition of Hb $A_{1c}$ has an immediate practical value. The quantification of this minor hemoglobin fraction is valuable in monitoring the control of diabetic patients, as has been noted in Koenig et al. in New England Journal of Medicine 295: 417–20 (1976). Currently available assays call for the column chromatographic separation of Hb $A_{1c}$ from the other hemoglobin components of the hemolysate. This is a tedious and not entirely accurate semi-quantitative method since only some 70–80% of the hemoglobin applied to the column is recovered.

The level of Hb $A_{1a}$ + Hb $A_{1b}$ in hemolysates is generally less than 50% that of Hb $A_{1c}$ and, under assay conditions, their contribution to the blocking of anti-$A_{1c}$ is less than 10% of a comparable amount of Hb $A_{1c}$. It is therefore unlikely that these two minor glycohemoglobins contribute significantly to the radioimmunoassay value of Hb $A_{1c}$. In 14 hemolysates in which Hb $A_{1c}$ was assayed by RIA and all three glycohemoglobins were measured by chromatography, correction of the RIA values for the contribution by Hb $A_{1a+b}$ did not significantly affect the correlation between the two methods.

The RIA can be standardized with purified Hb $A_{1c}$ and Hb $A_o$ and is not subject to error due to the selective loss of one or another hemoglobin fractions from the samples. This method offers a number of advantages over available techniques. The assay is specific and reproducible, yet simple enough to permit the processing of 30 or more samples under identical conditions within a working day. It should find ready application in the study of diabetes in man, as well as in experimental animals.

Hb $A_o$ and Hb $A_{1c}$ are immunologically identical except for a single antigenic determinant. Therefore, following the adsorption of anti-Hb $A_{1c}$ with Hb $A_o$, the residual specific antibody has a low titer and affinity. This inherent problem has been overcome in the present system by two modifications of the usual RIA method: First, the antibody is incubated sequentially with the test and index antigens, rather than with a mixture of the two, thus maximizing the blocking of the antibody by the test antigen. Second, the incubation with the index antigen is generally limited to about 0.5 hour, rather than overnight, so that the displacement of antigen from the low-affinity antibody is minimized.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. All temperatures are set forth uncorrected in degrees Celsius; unless otherwise indicated, all pressures are ambient and all parts and percentages are by weight.

EXAMPLE 1

Preparation of Hemoglobin Samples

Blood samples were obtained from normal individuals and from patients with diabetes mellitus. Hemolysates were made from saline washed red cells by hypotonic lysis. Stroma was removed by centrifugation. Total hemoglobin concentration was measured as cyanmethemoglobin, using the method of Cartwright described with "Diagnostic Laboratory Hematology", 4th edition, Grune and Stratton, New York (1972). Assay of the Hb $A_{1c}$ fraction was performed as previously described by Trivelli et al.

The main hemoglobin fraction $A_o$ and the minor hemoglobins $A_{1a}$, $A_{1b}$ and $A_{1c}$ were isolated and purified by column chromatography from the erythrocytes of normal volunteers following the procedures described in New England J. Med. 284: 353–357 (1971) and Proc. National Acad. Sci. USA 72: 3687–91 (1975). The Hb $A_o$ fraction thus isolated was then stripped of ionically-bound organic phosphates by dialysis in vacuum-expanded bags against 0.5 M NaCl—0.01 M sodium phosphate buffer, pH 7.0. The stripped Hb $A_o$ was then repurified by the above column chromatographic procedure. This process is necessary to prevent small amounts of Hb $A_{1b}$—like species from forming in the Hb $A_o$ fraction; see V. J. Stevens et al. in J. Biol. Chem. 252: 2998–3002 (1977). A similar chromatographic method was used for the separation of mouse and dog glycohemoglobins except that the equilibrating and eluting buffers were 0.05 M sodium phosphate, 0.01 M KCN, with pH 6.68 for the dog and pH 6.78 for the mouse hemolysates. The components $A_{1a}$ and $A_{1b}$ were eluted in one peak. The glycoproteins were concentrated by vacuum dialysis. All purified hemoglobins were stored at $-20°$ C. in the PCG buffer described below.

For reduction with NaBH$_4$, each glycohemoglobin was dialyzed against 0.1 M sodium phosphate buffer, pH 7, and was subsequently reacted with a 200-fold molar excess of $NaBH_4$ at room temperature for one hour. The unreacted sodium borohydride was removed by dialysis. The synthesis of glycosylated dipeptides has been previously described by Koenig et al. in J. Biol. Chem. 252: 2992–97 (1977).

EXAMPLE 2

Preparation of Antibodies

A cheviot sheep was injected biweekly with 10 mg of purified human Hb $A_{1c}$ in 3 ml water and 2 ml Fruend's adjuvant. The first 8 injections utilized complete adjuvant and the five subsequent injections were with incomplete adjuvant. Each 5 ml injection was given into 25 intradermal sites. Following the 8th injection, 500 ml blood was removed from the sheep on each non-immunization week. The blood was left overnight at 4° C. and the serum was collected by centrifugation and stored at −85° C. This is referred to herein as the parent antiserum. This antiserum showed minimal difference in its reactivity with Hemoglobin $A_{1c}$ and Hemoglobin $A_o$. This difference was amplified with progressive absorption of the antiserum with Hb $A_o$ at the expense of a considerable fall in antibody titer. Approximately 10% of the initial titer was retained as specific anti-$A_{1c}$. Anti-A, the fraction of the parent antiserum that was retained on and eluted with the Hb $A_o$ immunoabsorbent, did not discriminate between Hb $A_{1c}$ and Hb $A_o$.

In the reaction of human hemoglobin A fractions with anti-$A_{1c}$, the absorbed antiserum clearly distinguishes Hb $A_o$ from its glycosylated derivatives. Of the latter, Hb $A_{1c}$ is most effective in blocking the antiserum; Hb $A_{1a}$ and Hb $A_{1b}$ show about 5% and 10% of its reactivity, respectively. The four hemoglobin A fractions are equally effective in blocking anti-A, which recognizes only the determinants unrelated to the carbohydrate ligand.

Treatment of the hemoglobins with $NaBH_4$ had no effect on their reaction with the non-specific anti-A, but it led to a striking reduction of reactivity with anti-$A_{1c}$, as shown in the following Table 1:

TABLE 1
THE SPECIFICITY OF BOROHYDRIDE REDUCTION FOR THE IMMUNODOMINANT DETERMINANT OF GLYCOHEMOGLOBINS

| | Maximal blocking of | |
|---|---|---|
| | Anti-$A_{1c}$ | Anti-A |
| Hb $A_{1a}$, unmodified | 78% | 97% |
| Hb $A_{1b}$, unmodified | 90% | 94% |
| Hb $A_{1c}$, unmodified | 98% | 91% |
| Hb $A_{1a}$, reduced | 18% | 94% |
| Hb $A_{1b}$, reduced | 24% | 89% |
| Hb $A_{1c}$, reduced | 19% | 94% |

The common antigenic determinants of hemoglobin (Column 2) are present in all three glycohemoglobins and are not affected by borohydride reduction. The specific glycohemoglobin determinant (Column 1) is most reactive in Hb $A_{1c}$, least so in Hb $A_{1a}$, and is significantly altered by borohydride reduction.

EXAMPLE 3

Preparation of Radioimmunoassay Reagents

The following reagents were prepared:

TBS: (tris-buffered saline) 0.05 tris-hydroxymethylaminomethane, 0.1 M NaCl, pH 8.3.

PBS: (phosphate buffered saline) 0.05 M sodium phosphate, 0.1 M NaCl, pH 7.0.

BGG: 2% bovine gamma globulin in TBS. This was used for the final dilution of all antisera for the radioimmunoassay.

PCG: (phosphate-cyanide-glycerol) 0.1 M sodium phosphate, 1.5 mM KCN in 40% glycerol, pH 7.0. This buffer was used for storing hemoglobin samples at −20° C., at which temperature they did not freeze. The storage stability of the samples was considerably enhanced by this means.

Ammonium sulfate: Saturated solution, adjusted to pH 7.0 with 5 M NaOH.

Antisera: An aliquot of the parent antiserum was repeatedly absorbed with agarose-linked Hb $A_o$ according to the method of Javid and Liang, described in J. Lab. Clin. Med. 82: 991–1002 (1973) and the specificity of the residual antibodies for Hb $A_{1c}$ was monitored as described below. The final preparation is designated anti-$A_{1c}$. The cross-reacting antibodies which bound to the immunoabsorbent were eluted with 0.2 M glycine, pH 2.8, and dialyzed against PBS. This preparation is referred to as anti-A since it is directed against those antigenic determinants common to Hb $A_{1c}$ and Hb $A_o$.

Each antiserum was calibrated against the index antigen following the procedure of Javid and Yingling described in J. Clin. Invest. 47: 2290–2296 (1968). For the parent antiserum and anti-A, the equivalences (micrograms Hb $A_{1c}$ bound/ml antiserum) were 1120 micrograms/ml and 185 micrograms/ml, respectively. These antisera were diluted in BGG to a final titer of 0.375 micrograms/ml. Equivalent amounts of index antigen were used for these antisera. The calibration curve for anti-$A_{1c}$ did not show a sharp end point because of the low affinity of the antiserum; the equivalence was estimated at 100 micrograms/ml. This antiserum was diluted to a titer of 2 micrograms/ml and used in three-fold excess over the index antigen. This yielded lower values for "Antibody Control" (see below) and more reproducible results but did not alter the values obtained.

For an index antigen, purified Hb $A_{1c}$ was iodinated with $125_I$ by the chloramine-T method of McConahey and Dixon, described in the International Archives of Allergy and Immunology 29: 185–189 (1966). The hemoglobin, as obtained by chromatography, is in a buffer containing cyanide. This ion interferes with the oxidation of iodide to iodine. Prior to iodination, the cyanide must be removed from the sample by gel filtration or by dialysis. The specific activity of the preparations was about 1 mCi/mg. The antigen was stored as a 0.3 mg/ml solution in PCG buffer. Immediately prior to use, the antigen was diluted 100-fold in sheep hemoglobin (1 mg/ml).

Test hemoglobins: For studies of the primary inhibition of antisera, purified hemoglobins were used in amounts ranging from 0.025 to 25 microgram. A set of mixtures of purified Hb $A_{1c}$ and Hb $A_o$ were used as primary standards for the quantitative assay. These contained 0.0, 1.5, 3.6, 7.5, 9.0, 10.0, 12.0 and 15.0% Hb $A_{1c}$ in Hb $A_o$. Stock solutions, 2 mg/ml, were diluted 1:20 in sheep hemoglobin (0.5 mg/ml) and 50 microliters of each mixture was used to construct the standard curve. Assay unknowns were hemolysates from normal and diabetic donors. These were diluted from stock solutions as described for the standards.

EXAMPLE 4

Radioimmunoassay (RIA) Testing:

All antisera and hemoglobins were diluted as outlined in the preceding section. Reactions were carried out in triplicate for the standards, and in duplicate for other test hemoglobins. The assay consists of three stages Stage 1: The reaction mixture which contained 200 microliters antiserum and 50 microliters test hemoglobin was incubated at room temperature for 30 minutes. Each experiment included two controls. In the "Antibody Control" the test hemoglobin was replaced by the sheep hemoglobin diluent, permitting full reaction between antibody and index antigen in the subsequent stage. In the "Antigen Control" the antibody was omitted (only the BGG diluent was used) to establish the inherent solubility of the free index antigen under the assay conditions.

Stage 2: Freshly diluted index antigen was added to each reaction mixture and further incubated at room temperature for 30 minutes.

Stage 3: TBS, 1.45 ml and ammonium sulfate, 1 ml, were added sequentially to each tube with thorough vortex mixing. After ½ hours at 4° C. the precipitated immune complexes were sedimented at 1,000×G for 10 minutes. Supernatant radioactivity was calculated from the counts in 1 ml and was expressed as the percent of total counts.

Percent Blocking of the Antiserum is defined as:

$$(T-B)/(A-B) \times 100$$

wherein the symbols are the percent supernatant counts for test hemoglobins (T), antigen control (A), and antibody control (B).

For assay purposes, a standard curve was constructed by plotting the percent blocking for each of the primary standards against its known fractional content of Hb $A_{1c}$ and Hb $A_o$.

EXAMPLE 5

Reaction with glycosyl dipeptides

A number of glycosylated derivatives of the N-terminus of the human hemoglobin beta-chain were tested for their ability to inhibit the primary reaction between Hb $A_{1c}$ and its specific antibody. None of the compounds tested showed significant blocking activity, even in up to 1,000-fold molar excess, as shown in Table 2:

TABLE 2

MAXIMAL BLOCKING OF ANTI-$A_{1c}$ ANTISERUM BY SYNTHETIC GLYCOPEPTIDES

| Substance | Moles Added | % Blocking |
|---|---|---|
| Hb $A_{1c}$ | $7 \times 10^{-11}$ | 95% |
| Hb $A_{1c}$, reduced 1-deoxy | $7 \times 10^{-11}$ | 20% |
| Mannosyl-valine, reduced 1-deoxy | $2 \times 10^{-9}$ | 6% |
| Mannosyl-valine, reduced 1-deoxy | $1 \times 10^{-9}$ | 6% |
| Galactosyl-valine, reduced 1-deoxy | $2 \times 10^{-9}$ | 6% |
| Galactosyl-valine, reduced 1-deoxy | $2 \times 10^{-7}$ | 8% |
| Glucosyl-valyl-histidine, reduced 1-deoxy | $2 \times 10^{-9}$ | 9% |
| Glucosyl-valyl-histidine, reduced | $2 \times 10^{-8}$ | 9% |

There is no significant blocking of the antiserum by glycopeptides in up to 1,000-fold molar excess over totally blocking amounts of Hb $A_{1c}$ or partially reactive reduced Hb $A_{1c}$.

EXAMPLE 6

Species Cross-Reactivity

The Hb $A_o$, $A_{1a+b}$ and $A_{1c}$ components of dog and mouse hemoglobin were tested for cross reactivity in the RIA system. The reaction of these hemoglobins with anti–$A_{1c}$ is qualitatively analogous to that of their human counterparts. The mouse and dog Hb $A_{1c}$ have about 15% of the reactivity of the human fraction for half-maximal blocking of anti–$A_{1c}$. The $A_o$ component in each species is inactive, while the hemoglobins $A_{1a+b}$ have intermediate reactivities.

EXAMPLE 7

Quantitative assay of Hb $A_{1c}$ by RIA:

The relation between the percent Hb $A_{1c}$ in the standard mixtures, and the percent blocking of anti–$A_{1c}$ was plotted as a standard curve. Mean and standard deviation for 9 consecutive experiments performed over a 40-day period with the same index antigen were included. There was no progressive shift of the curve in any direction; the range of values for each sample represents the inherent limit of reproducibility for the method. The y-intercept of the curve shows residual cross reactivity of the anti–$A_{1c}$ with Hb $A_o$.

Assay values for hemolysates with more than 9% Hb $A_{1c}$ fell on the upper, shallower slope of the standard curve. In these instances the hemolysates were diluted with an equal amount of Hb $A_o$; the percent blocking then fell on the steeper portion of the curve. The corresponding percent Hb $A_{1c}$ was doubled to correct for the two-fold dilution of the hemolysate and more reproducible results were thus obtained. It was found more convenient to include one such dilution with every hemolysate assayed, rather than perform a second assay for those specimens with high Hb $A_{1c}$.

Thirty-three hemolysates were assayed for Hb $A_{1c}$ by both the RIA and the column method. In general, higher values are obtained by RIA. The regression line for these data is $y = 1.16 \times 0.15$ with a coefficient of determination $r^2 = 0.72$. In order to evaluate the source of the discrepancy between the two methods, the following experiment was performed: Two hemolysates, assayed by RIA to have 4.5 and 12.4% Hb $A_{1c}$, respectively, were mixed in 10 different proportions. The original hemolysates and the mixtures were assayed in a blinded fashion by both the RIA and the column methods, and the results were compared with the values of the $A_{1c}$ calculated from the composition of the mixtures. An excellent correlation was observed for the RIA with the regression formula $Y = X + 0.06$, and $r^2 = 0.99$. By contrast, the regression formula for the chromatographic analysis of the same mixtures, using the column values for the original hemolysates for the calculations, was $y = 1.025 X - 0.81$, and $r^2 = 0.87$. Thus, the RIA method has a high degree of internal consistency and is linear throughout the range examined.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

We claim:

1. Antibodies against human hemoglobin $A_{1c}$ which are substantially free of cross-reactivity against the human hemoglobins $A_o$, $A_{1a}$ and $A_{1b}$.

2. Antibodies according to claim 1 which are obtained by immunization of an animal whose metabolism does not naturally produce Hemoglobin $A_{1c}$.

3. Antibodies according to claim 2, wherein said animal is a sheep.

4. A method for quantitatively detecting the presence of hemoglobin $A_{1c}$ in a blood sample, which comprises reacting said sample with the antibody according to claim 1 and determining the presence of an antigen-antibody complex by radioimmunoassay by reacting the resultant product with radioactively labeled indexed antigen.

5. A method according to claim 4, wherein reaction with the index antigen is effected by incubation at room temperature to about 37° C. for about 0.5 hour.

6. A method for assessing carbohydrate intolerance in a living mammal, which comprises quantitatively detecting the presence of hemoglobin $A_{1c}$ in a blood sample according to any one of claims 4 or 5, and evaluating the hemoglobin $A_{1c}$ levels in excess of about 6% as an indication of carbohydrate intolerance.

7. A diagnostic test kit for quantitatively assessing hemoglobin $A_{1c}$, comprising a container of the antibody of claim 1 in combination with a container of radioactively labeled, substantially pure hemoglobin $A_{1c}$ antigen control.

8. A diagnostic kit according to claim 7, wherein the radioactive labeling is with iodine 125.

9. A method for preparing antibodies according to claim 1, which comprises administering an antigenically effective amount of purified hemoglobin $A_{1c}$ antigen to an animal capable of producing antibodies thereto and collecting said antibodies from the animal.

10. A method according to claim 9, wherein said animal is one whose metabolism does not naturally produce hemoglobin $A_{1c}$.

11. A method according to claim 10, wherein said animal is a sheep.

* * * * *